United States Patent [19]

Naguib et al.

[11] Patent Number: 5,141,943
[45] Date of Patent: Aug. 25, 1992

[54] 5-BENZYL BARBITURATE DERIVATIVES

[75] Inventors: Fardos N. M. Naguib; Mahmoud H. el Kouni, both of Providence; Raymond Panzica, Narragansett; Sungman Cha, Providence, all of R.I.

[73] Assignee: Brown University Research Foundation, Providence, R.I.

[21] Appl. No.: 508,363

[22] Filed: Apr. 12, 1990

[51] Int. Cl.$^5$ .................. C07D 239/02; A01N 43/54
[52] U.S. Cl. ........................ 514/270; 514/271; 544/299; 544/301; 544/302; 544/306
[58] Field of Search ............. 544/299, 301, 302, 306; 514/270, 271

[56] References Cited

U.S. PATENT DOCUMENTS

| | | | |
|---|---|---|---|
| 3,282,921 | 11/1966 | Verheyden et al. | 260/211 |
| 3,687,931 | 8/1972 | Verheyden et al. | 260/211 |
| 3,755,295 | 8/1973 | Verheyden et al. | 260/112 |
| 3,775,397 | 11/1973 | Etzold et al. | 260/211 |
| 3,817,982 | 6/1974 | Verheyden et al. | 260/211 |
| 4,071,680 | 1/1978 | Cook | 536/23 |
| 4,093,715 | 6/1978 | Lin et al. | 424/180 |
| 4,128,639 | 12/1978 | Lin et al. | 424/180 |
| 4,210,638 | 7/1980 | Greer | 424/180 |
| 4,230,698 | 10/1980 | Bobek et al. | 424/180 |
| 4,331,662 | 5/1982 | Eckstein et al. | 424/180 |
| 4,604,382 | 8/1986 | Lin et al. | 514/49 |
| 4,681,933 | 7/1987 | Chu et al. | 536/23 |

FOREIGN PATENT DOCUMENTS 1171434  11/1969  United Kingdom .

OTHER PUBLICATIONS

Naguib et al., "Biochemical Pharmacology", 39(13) 2195-2201, 1987.
D'Yachkov et al., Chemical Abstract vol. 87, #200589g 1977, p. 648.
Niedzwicki et al., paper, vol. 32 *Biochemical Pharmacology*, pp. 339-415 1983.
Goodman and Gilman's *The Pharmacological Basis of Therapeutics* (1990).
Sommadossi et al., Antimicrobial Agents and Chemotherapy, vol. 32, No. 7, pp. 997-1001 (Jul. 1988), Uridine Reverse . . . .
Horwitz, vol. 29, J. Org. Chem., pp. 2076-2078 (1964), Nucleosides. V. The Monomesylates . . . .
Lin et al., vol. 21, J. Med. Chem., pp. 109-112 (1978), Synthesis and Biological Activity . . . .
Lin et al., vol. 36, Biochem. Pharmacol., pp. 311-316 (1987), Antiviral Activity of . . . .
Schinazi et al., Interscience Conference on Antimicrobial Agents and Chemotherapy Abstract #369 (1987), Selective In Vitro . . . .
Tatsumi et al., Jpn. J. Caner Research (Gann), vol. 78, pp. 748-755 (Jul. 1987), Inhibitory Effects of . . . .
Dyschinsky et al., vol. 79, J. Amer. Chem. Soc., pp. 4559-4560 (1957).
Heidelberg in Antineoplastic and Immune . . . (Sartorelli et al., ed.s, Spinger-Verlag, Heidelberg, pp. 193-231 (1975)).
Niedzwicki et al., vol. 31, Biochemical Pharmacology, No. 10, pp. 1857-1861 (1982), 5-Benzylacyclouridine and . . . .
Monks et al., vol. 32, Biochemical Pharmacology, No. 13, pp. 2003-2009 (1983), Effect of 5-Benzylacyclouridine . . . .
Darnowski et al., vol. 45, Cancer Research, pp. 5364-5368 (1985), Tissue-specific Enhancement . . . .
Naquib et al., vol. 36, Biochemical Pharmacology, No. 13, pp. 2195-2201 (1987), New Analogues of . . . .
Conrad et al., vol. 34 Ber., pp. 1339-1346 (1901), Condensation von . . . .
Sekiya et al., vol. 17, Chem. Pharm., Bull., pp. 738-746 (1969), Formic Acid Reduction . . . .
Speer et al., vol. 21, Org. Syn., pp. 5-8 (1941).
Sekiya et al., vol. 17, Chem. Pharma., Bull., pp. 747-751 (1969), Formic Acid Reduction IV . . . .
Tanaka et al., vol. 36, Chem. Pharm., Bull., pp. 60-69 (1988), 5-Arylidene 1,3-. . . .
Robins et al., vol. 60, Can. J. Chem., pp. 547-553 (1982), Nucleic Acid Related . . . .
Levine et al., vol. 19, Biochemistry, pp. 4993-4999 (1980), Inhibition of Orotidine-5'. . . .
Harnden et al., vol. 4, pp., Nucleosides and Nucleotides, pp. 465 476, (1985) Synthesis of Analogues . . . .
MarCoss et al., vol. 26, Chem. Scripta, pp. 113-121 (1986), Synthetic, Biochemical and . . . .
Kim et al., Chem. Lett., pp. 1045-1048, (1988), Efficient Synthesis of . . . .
Pelter et al., vol. 3, Comprehensive Org. Chem., pp. 760-772 (D. N. Jones ed., Pergamon Press (1976)).
Boss et al., vol. 15, Agnew Chem. Inter. Ed. Engl., pp. 558-559 (1976).
Bayley et al., Tetrahedron Lett., No. 39, pp. 3633-3634 (1978), A Selective Reagent . . . .
Rolla, vol. 47, Org. Chem., pp. 4327-4329 (1982), Sodium Borohydride Reactions . . . .
Chu et al., vol. 24, J. Heterocyclic Chem., pp. 1651-1656 (1986), Synthesis of Variants of . . . .
Bradford, vol. 72, Analyt. Biochem., pp. 248-254 (1976), A Rapid and Sensitive . . . .
Griffith, vol. 55, Ann. Rev. of Biochem., pp. 866-868 (1986).
Hammer et al., vol. 31, Antimicrobial Agents and Chemotherapy, pp. 1046-1050 (1987) Synergistic Activity of . . . .

*Primary Examiner*—Mukund J. Shah
*Assistant Examiner*—Y. N. Gupta
*Attorney, Agent, or Firm*—Thomas J. Engellenner

[57] ABSTRACT 5-benzyl barbiturate compounds for use as water-soluble uridine phosphorylase inhibitors are disclosed. These compounds are useful for reducing the toxicity and anemia induced by antiviral drugs such as AZT, as well as for potentiating anticancer drugs and combatting their host-toxicity.

38 Claims, No Drawings

5-BENZYL BARBITURATE DERIVATIVES

BACKGROUND OF THE INVENTION

This invention relates to the synthesis and measurement of novel benzyl barbiturate derivatives useful as uridine phosphorylase inhibitors in cancer and viral therapies.

It is known in the art that uridine phosphorylase inhibitors possess a number of clinically useful attributes. For example, uridine phosphorylase inhibitors have been proposed as means to increase the selectivity and efficacy of various uracil and uridine derivatives in cancer chemotherapy. In another application (U.S. application Ser. No. 180,525), uridine phosphorylase inhibitors have been proposed recently as rescue agents for reducing the toxicity of antiviral agents such as 3'-azido-3'deoxythymidine (AZT). To be useful, the uridine phosphorylase inhibitors should be potent, specific, and non-toxic, and readily soluble in aqueous solutions buffered within the physiological pH range. In addition, the compounds should also be easy to make and to use.

In the field of cancer chemotherapy, the use of halogenated pyrimidine bases such as 5-fluorouracil (5-FUra), and halogenated pyrimidine nucleosides such as 5-fluoro-2'-deoxyuridine (5-FdUrd) as chemotherapeutic agents is well documented in the art (Heidelberger, C., in *Antineoplastic and Immune Suppressive Agents* Part II, A. C. Sartorelli and D. G. Jones ed.s, pp. 193–231, (Springer-Verlag, Heidelberg, 1975)). However, the halogenated pyrimidine nucleosides are rapidly degraded to their respective pyrimidine bases, reducing their effectiveness against the cancer tissue they are meant to treat. Moreover, the pyrimidine bases, like 5-fluorouracil, are generally more toxic to the host (non-tumor) tissue.

In recent years investigators have found that uridine phosphorylase inhibitors can increase the efficacy of both chemotherapeutic pyrimidine nucleosides and bases.

In the case of halogenated pyrimidine nucleosides, it is known that the catabolic pathway of these compounds is the same as that of uridine. It is also known that there is little functional thymidine phosphorylase in many tumor cells. As such, the first step in the catabolic pathway in these cells relies primarily on uridine phosphorylase. Inhibiting this enzyme in tumor cells inhibits the catabolism of the agents in tumor tissue, thereby increasing their effectiveness. In host tissue, the halogenated pyrimidine nucleosides can still be catabolized to their pyrimidine counterparts by the action of thymidine phosphorylase.

In the case of halogenated pyrimidine bases like 5-fluorouracil, the agent can compete with cellular uridine and its nucleotides for incorporation into RNA and DNA. However, uridine phosphorylase inhibitors increase the plasma uridine concentration (Monks A. et al., vol. 32, *Biochem. Pharmac.*, pp. 2003–2009 (1983)), and availability of uridine for salvage by host tissue, and increase the tissue pools of uracil nucleotides. The increased intracellular uridine concentration can reduce the toxicity of halogenated compounds in host tissue. Moreover, Darnowski et al. (vol. 45, *Cancer Res* pp. 5364–5368 (1985)) have shown that the addition of a phosphorylase inhibitor selectively increases the ability of host tissue to salvage uridine. This tissue-specific enhancement of uridine utilization is of particular importance for chemotherapies with 5-fluorouracil.

Another application for uridine phosphorylase inhibitors lies in the protection against host toxicity of antiviral agents. For example, viral therapies for patients infected with the human immunodeficiency virus (HIV), and/or suffering from the acquired immune deficiency syndrome (AIDS), have typically involved the administration of an "antiviral" pyrimidine nucleoside, such as, AZT, (3'-azido-3'-deoxythymidine). These "antiviral" agents function by inhibiting the reverse transcriptase enzyme of the HIV and reducing the cytopathic effects of the virus.

However, the utility of these antiviral pyrimidine nucleosides has been limited by their toxic effects on uninfected cells. Prolonged administration of AZT or related agents can have severe side effects. One common and serious complication of AZT therapy is the suppression of bone marrow growth in the patient (specifically, granulocyte-macrophages and erythrocyte progenitor cells), which leads to severe anemia. This complication has generally limited the dosage or duration of therapy that can be implemented.

Recently, it has been shown that uridine and, to a lesser extent, cytidine can reverse the toxic effects of AZT in human bone marrow progenitor cells (HBMP) without affecting the inhibitory activity of AZT in viral infected cells. See, Somadossi et al., vol. 32, *Antimicrob. Agents Chemother.* pp. 997–1000 (1988). The mechanism for this "rescuing" ability of uridine is unclear at the present. Unfortunately, because of the body's efficient uridine catabolism, clinical implementation of uridine "rescue" regimens requires administering high doses of uridine. Such high doses can cause toxic side effects, such as phlebitis and pyrogenic reactions.

Viral therapies based on the combination of AZT (or the like) and uridine phosphorylase inhibitors have been suggested by one of the present coinventors and a colleague as an alternative to the uridine "rescue" regimen. See commonly owned, pending U.S. patent application Ser. No. 180,525, filed Apr. 25, 1988, herein incorporated by reference. In this application, uridine phosphorylase inhibitors (UPIs) maintain an effective level of the body's plasma uridine sufficient to "rescue" uninfected cells, without requiring the administration of large doses of uridine.

A number of synthetic uridine phosphorylase inhibitors have been proposed by researchers, including a variety of substituted acyclouridines. See, for example, Niedzwicki et al., vol. 31, *Biochem. Pharmac.* p. 1857 (1982), and Naguib et al., vol. 36, *Biochem. Pharmac.* p. 2195 (1987), as well as U.S. Pat. No. 4,613,604, issued to Chu et al.

However, while some of these compounds have proven to be good inhibitors of uridine phosphorylase, many of the acyclouridines are not very water soluble, and in addition, are difficult and expensive to synthesize. Efforts to increase the water solubility of these compounds have met with only limited success (Naguib et al., vol. 36, *Biochem. Pharmac.* p. 2195 (1987)). Water solubility is essential for practical chemotherapy and antiviral treatments, in order to provide intravenous administration at physiological pH ranges and to allow formulation of reasonable administering volumes. Unfortunately, acyclouridines such as BAU, BBAU, and HM-BBAU are soluble only to about 1 mM in water at room temperature. Administration of a physiologically useful dose can require dilution of these compounds into undesirably large volumes. Although the compounds could be dispersed in an oil and taken orally, this method of administration is not preferred initially, as it is difficult to predict by this method how well the compounds will be absorbed as they will have a first pass effect, i.e., ineffective by oral route. Therefore a need exists for new uridine phosphorylase inhibitor compounds that are easier and more cost-efficient to produce in large quantities, more potent, and more soluble in aqueous solutions.

Accordingly, it is an object of this invention to provide new compounds useful as uridine phosphorylase inhibitors and which can be administered in viral and cancer chemotherapies to reduce toxicity in normal cells. Another object of the invention is to provide a method for reducing the anemia and bone marrow suppression caused by the administration of pyrimidine nucleoside analogues in the treatment of viral infections such as HIV, and HIV-related illnesses such as AIDS, and to provide pharmaceutical preparations for such purposes. Yet another object is to increase the efficacy of cancer chemotherapeutic compounds, as well as to reduce the toxicity of these compounds in normal tissues, and to provide pharmaceutical preparations for these purposes.

These and other objects and features of the invention will be apparent from the description and claims which follow.

SUMMARY OF THE INVENTION

Previously unknown derivatives of 5-benzyl barbiturate have been synthesized and tested as inhibitors of uridine phosphorylase. The new compounds are specific and potent inhibitors of uridine phosphorylase. Moreover, they are water soluble and their synthesis is cost-efficient. These uridine phosphorylase inhibitors are useful for reducing the toxicity and/or potentiating the efficacy of anti-cancer drugs, as well as for reducing the toxicity and anemia induced by antiviral drugs such as AZT.

The discovery that the newly synthesized 5-benzyl barbiturate derivatives inhibit uridine phosphorylase is novel. While the synthesis of 5-benzyl barbiturate and 5-benzylidene barbiturate are well described in the art, (Conrad, R. vol. 34, *Ber.*, p. 1340 (1901), and Seyika, M. et al., vol. 17, *Chem. Pharm. Bull.*, pp. 738-346 (1969)), a physiological use for these compounds has never been investigated. Moreover, in 1987 Tatsumi et al. showed that 5-alkylated or 5-halogenated barbiturates do not affect the activity of uridine phosphorylase (See Tatsumi et al., vol. 78, *Japanese J Cancer Res* pp. 748-755 (1987)).

The 5-benzyl and 5-benzylidene barbiturate derivatives of this invention are defined by the following general formula:

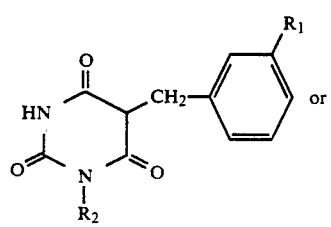

-continued

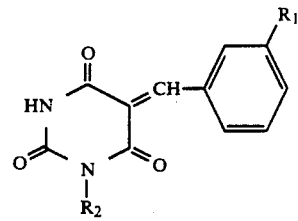

where $R_1 = OCH_3$, or $OCH_2C_6H_5$, $R_2 = H$, or an acyclo tail of the general formula:

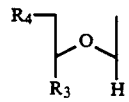

where $R_3 = H$, $CH_2OH$, or $CH_2NH_2$ and $R_4 = OH$, $NH_2$, or $OCOCH_2CH_2CO_2H$ As used herein, the 5-benzyl barbiturate derivatives of this invention include their 5-benzylidene counterparts. The 5-benzyl barbiturate derivatives of the present invention are particularly advantageous because they are the most potent and specific inhibitors of uridine phosphorylase known. They are water soluble, and they do not appear to affect normal cell growth adversely. Moreover, they do not interfere with the activity of antiviral or anticancer drugs.

In antiviral treatments, the 5-benzyl barbiturate compounds of this invention are useful for reducing the nucleoside toxicity and anemia caused by antiviral therapies comprising antiviral pyrimidine nucleoside compounds such as, for example, AZT. The 5-benzyl barbiturates of the present invention may be administered in combination with these antiviral therapies, either together or sequentially. Because the 5-benzyl barbiturate compounds of the present invention are water-soluble, they can be administered intravenously in saline solutions or saline solutions buffered within the physiological range. Buffers such as phosphate, bicarbonate, or citrate can be readily used for this purpose.

The 5-benzyl barbiturates of the present invention may also be administered with low levels of uridine in antiviral therapy regimens in order to increase the plasma uridine levels in uninfected cells.

As used herein, the term "antiviral pyrimidine nucleoside compound" is intended to encompass all compounds exhibiting antiviral activity and having the following general structures:

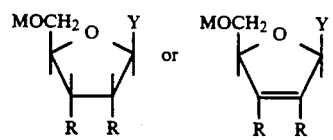

where Y is a heterocyclic pyrimidine base; the 5-carbon monosaccharide may be modified at its 2' and 3' position (R); and M is H, a pharmaceutically acceptable salt, or a mono-, di-, or triphosphate. Antiviral agents useful in the combination therapies disclosed herein include 3'-azido-3'-deoxythymidine (AZT), -continued

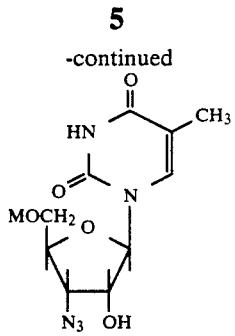

3'-azido-2',3'-dideoxyuridine (AZd₂U),

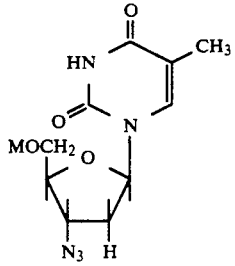

2',3' dideoxycytidin-2'ene (d4C),

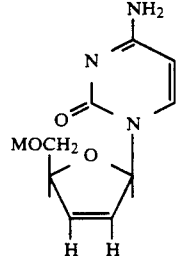

2',3' dideoxythymidin-2'ene (d4T), and

3'-fluoro-2'-deoxythymidine (FdT)

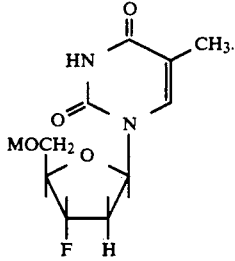

Further information on the synthesis of these compounds and their antiviral activities can be found in U.S. Pat. No. 3,282,921 issued to Verheyden et al. on Nov. 1, 1966; U.S. Pat. No. 3,687,931 issued to Verheyden et al. on Aug. 29, 1972; U.S. Pat. No. 3,755,295 issued to Verheyden et al. on Aug. 28, 1973; U.S. Pat. No. 3,775,397 issued to Etzold et al. on Nov. 27, 1973; U.S. Pat. No. 3,817,982 issued to Verheyden et al. on Jun. 18, 1974; U.S. Pat. No. 4,071,680 issued to Cook on Jan. 31, 1978; U.S. Pat. No. 4,093,715 issued to Lin et al. on Jun. 6, 1978; U.S. Pat. No. 4,128,639 issued to Lin et al. on Dec. 5, 1978; U.S. Pat. No. 4,210, 638 issued to Greer on Jul. 1, 1980; U.S. Pat. No. 4,230,698 issued to Bobek et al. on Oct. 28, 1980; U.S. Pat. No. 4,331,662 issued to Eckstein et al. on May 25, 1982; U.S. Pat. No. 4,604,382 issued to Lin et al. on Aug. 5, 1986; U.S. Pat. No. 4,681,933 issued to Chu et al. on Jul. 21, 1987; Horwitz, vol. 29 *J. Org. Chem.* pp. 2076-2078 (1964); Lin et al., vol. 21 *J. Med. Chem.* pp. 109-112 (1978); Lin et al., vol. 36 *Biochem Pharmacol.* pp. 311-316 (1987); and Schinazi et al. *Interscience Conference on Antimicrobial Agents and Chemotherapy* Abstract #369 (1987), herein incorporated by reference.

As potentiators for anticancer halogenated pyrimidine compounds, the 5-benzyl barbiturates of the present invention may be administered in conjunction with 5-fluorouracil or any of the halogenated uridines in established cancer therapies. The 5-benzyl barbiturates are particularly effective in potentiating halogenated uridine compounds in tumors having low or no thymidine phosphorylase activity. Preferably, the 5-benzyl barbiturate compounds of the present invention are administered prior to the anticancer compounds or at the same time as the anticancer compounds, but they may also or alternatively be administered later. Administering the barbiturate compounds of the present invention prior to the anticancer agent would inhibit the uridine phosphorylase enzyme and thereby prevent degradation of the anticancer agent.

The 5-benzyl barbiturates of the present invention may also be administered with low levels of uracil or uridine (about 30 mg to 250 mg/kg of body weight) in order to increase the levels of uridine in plasma and in non-tumor cells. The combination therapies of this invention will help maintain a level of uridine sufficient to prevent the toxicity of the anticancer pyrimidines.

As used herein, the term "halogenated uridine compound" refers to all compounds capable of inhibiting cancerous cell growth and having the following general structure:

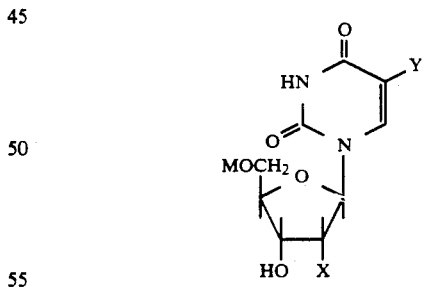

where Y is a halogen; X is H or OH; and M is H, a pharmaceutically acceptable salt, or a mono-, di-, or triphosphate. Halogenated uridine compounds useful in the combination therapies disclosed herein include: 5-fluorouridine (5-FUrd), 5-bromo-2'deoxyuridine, 5-iodo-2'deoxyuridine, and 5-fluoro-2'deoxyuridine, all of which may be obtained from Sigma Chemical Co., St. Louis, Mo. Further information on the synthesis and cancer therapeutic effects of halogenated uridines can be found in Dyschinsky et al., vol. 79, *J. Amer. Chem. Soc.*, p. 4559 (1957) and Heidelberger, C., in *Antineoplastic and Immunosuppressant Agents*, Part II, A. C. Sartorelli and D. G. Jones, ed.s, pp. 193-231, (Springer-Verlag, Berlin, 1975).

In addition to being useful in potentiating halogenated pyrimidine compounds used in cancer chemotherapies, it is anticipated that these 5-benzyl barbiturates also are useful in potentiating other pyrimidine therapeutic agents (e.g., 5-fluoro-cytosine) by protecting against host-toxicity.

It is also envisioned that the 5-benzyl barbiturates of this invention may be useful as part of therapies that treat uridine metabolism disorders. For example, $\beta$-alanine is a product of the uridine catabolic pathway. Excess production of $\beta$-alanine can lead to neurological disorders (hyper-$\beta$-alaninemia), and even death (Griffith, O. et al., vol. 55, Ann Rev. Biochem. pp. 875-878 (1986)). A uridine phosphorylase inhibitor capable of inhibiting uridine catabolism may limit $\beta$-alanine production, potentially ameliorating the effects of this disorder.

Effective dosages for the 5-benzyl barbiturates in the anticancer and antiviral therapies can be determined by routine experimentation. The objective of any administration of these compounds is to inhibit uridine phosphorylase. In cancer treatment, the inhibition of uridine phosphorylase increases the efficacy of the chemotherapeutic agent as well as limiting host-toxicity; in antiviral treatments, the inhibition of uridine phosphorylase reduces the nucleoside toxicity and anemia caused by the antiviral agent, thus allowing higher doses and/or prolonged regimens.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacterial and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption. For example, aluminum monosterate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from previously sterile-filtered solution thereof.

The active compounds may be administered parenterally or intraperitoneally. Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The active compounds also may be orally administered, for example, with an inert diluent or with an assimilable edible carrier, or they may be enclosed in hard or soft shell gelatin capsules, or they may be compressed into tablets, or they may be incorporated directly with the food of the diet. For oral therapeutic administration, the active compounds may be incorporated with excipients and used in the form of ingestible tablets, buccal tablets, troches, capsules, elixirs, suspension syrups, wafers, and the like. Such compositions and preparations should contain at least 0.1% of active compound. The percentage of the compositions and preparations may, of course, be varied and may conveniently be between about 2 to about 60% of the weight of the unit. The amount of active compounds in such therapeutically useful compositions is such that a suitable dosage will be obtained.

The tablets, troches, pills, capsules and the like may also contain the following: a binder, such as gum tragacanth, acacia, cornstarch, or gelatin; excipients, such as dialcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar, or both. A syrup or elixir may contain the active compounds sucrose as a sweetening agent, methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparations and formulations.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

DETAILED DESCRIPTION

The 5-benzyl barbiturate compounds of the present invention can be synthesized according to the reaction schemes and protocols described below.

EXAMPLE 1

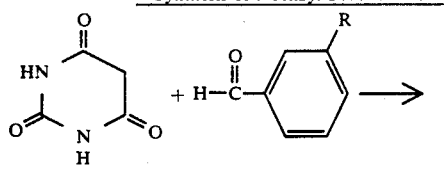

Synthesis of 5-benzyl Barbiturates

1

2. R = H
3. R = CH₃O
4. R = C₆H₅CH₂O

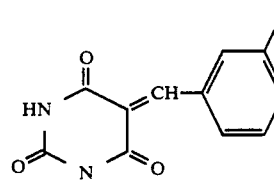

51 R = H
52 R = CH₃O
53 R = C₆H₅CH₂O

[H]

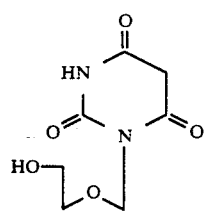

6 R = H
7 R = CH₃O
8 R = C₆H₅CH₂O

This protocol will produce 5-benzyl and 5-benzyloxybenzyl derivatives of barbituric acid and its stable 5-benzyl intermediates in good yield. The starting materials for this project are barbituric acid 1; and benzaldehyde 2, or either of two derivatives thereof: m-anisaldehyde 3, or m-benzyloxybenzaldehyde 4. All of these materials are commercially available from Aldrich Chemical Co., Milwaukee, Wis.

Condensation of barbituric acid 1 with the aldehydes 2-4, followed by reduction with sodium borohydride (ca. 1:3, starting material to NaBH₄), leads to their respective 5-benzyl derivatives in good yield. Synthesis of the arylidene intermediates can be carried out following known methodology (e.g., Speer et al., vol. 21, *Org. Syn.* pp. 5-8 (1941), and Sekiya et al., vol. 17 *Chem. Pharm. Bull.* pp. 747-751 (1969)), using a 10% excess of aldehyde. N-substituted arylidenes can be purified by silica gel column chromatography; unsubstituted intermediates (i.e., 5.1) can be recrystallized (as from alcohol).

Reduction of the 5-arylidene derivatives is carried out according to Tanaka et al., vol. 36, *Chem. Pharm. Bull.* pp. 60-69 (1988). Reduction of 5.1 and 5.2 requires some modification of the Tanaka protocol, as the resulting products are insoluble in chloroform. After quenching the reaction with water, the aqueous solution is acidified (ca. pH 3) with either Amberlite IR-120 H⁺ resin or hydrochloric acid. If resin is used, it is subsequently removed by filtration and washing. The filtrate and wash are then combined and concentrated. The precipitated solid is recrystallized from alcohol. In the case of the N-substituted arylidenes, a ratio of 1:5, starting material to NaBH₄ is used; for unsubstituted arylidenes, a ratio of 1:3 is used.

EXAMPLE 2

Synthesis of 5-benzyl barbiturates with acyclo tail [(2-ethoxy)methyl group]

This is a two-step process. Two alternative methods for producing these derivatives are presented. In protocol A, the acyclo tail is attached to barbituric acid first, followed by the addition of the benzyl groups. In protocol B, the acyclo tail is added to persilyated 5-benzyl derivatives which are then deprotected. Both methods form products in reasonable yield.

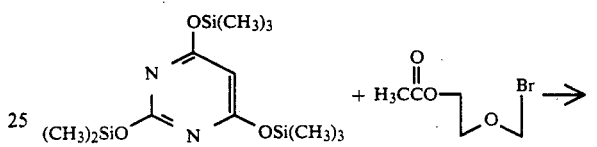

9

10

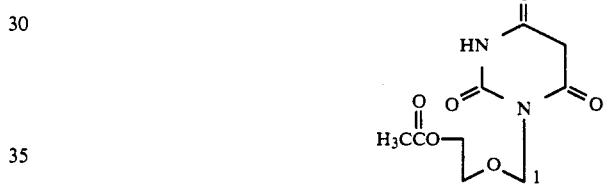

11

12

A. A persilylated derivative of barbituric acid 9 is alkylated at the 1 position with (2-acetoxyethoxy)-methyl bromide 10, following the procedure of Robins and Hatfield, vol. 60, *Can. J. Chem.* pp. 547-553 (1982), to provide the mono N-[(2-acetoxyethoxy)methyl] analogue 11. This procedure is modeled after the high-yield ribosylation of 9 disclosed in Levine et al., vol. 19, *Biochemistry* pp. 4993-4999 (1980). The analogue of 11 can be deprotected wih either NaOMe or NH₃/MeOH to furnish 1-(1-hydroxy-2-ethoxy)methyl barbituric acid 12.

Silylation of barbituric acid is carried out according to Harnden and Jarvest, vol. 4, *Nucleosides and Nucleotides.* pp. 465-476 (1985), using hexamethyldisilazane (HMDS), trimethylsilyl chloride and heat. The persilylated acid then is combined with 10 in acetonitrile.

Reactions are complete in about four hours. The mixture then is concentrated and purified by column chromatogaphy.

Either 11 or 12 can be used for the next synthesis sequence, leading to the desired derivatives 16–18, or their arylidene intermediates (13–15). If 12 is selected as the starting acyclonucleoside, the steps leading to 16–18 will follow the same procedures described for the synthesis of 6–8. If instead 11 is used, the 5-benzyl addition steps are the same as for 12, followed by deprotection of the acylated condensation products (13–15) by the method of Robins and Hatfield vol 60, *Can. J. Chem.* pp. 547–553 (1982).

Deprotection is carried out by stirring the compounds for two hours at room temperature, using sodium methoxide as the deblocking agent Upon completion of the reaction, the mixtures are acidified with Amberlite IR-120 H+resin and purified. It is worth mentioning that the acetyl group on 13–15 can provide greater organic solubility and, if retained at this point, would facilitate the borohydride reduction step. In this case, deprotection would follow the reduction step.

B. An alternative pathway leading to the target acyclonucleosides (16–18) also is possible. Here silyated bases of the 5-benzyl derivatives (6–8) are alkylated with 10 followed by deprotection. Persilyation of 6–8 follows the procedure described for 9, and deprotection occurs by the methods described above for 13–15.

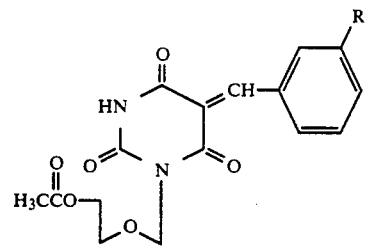

13 R = H
14 R = CH$_3$O
15 R = C$_6$H$_5$CH$_2$O

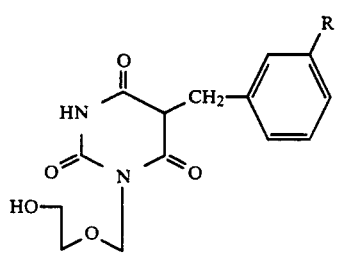

16 R = H
17 R = CH$_3$O
18 R = C$_6$H$_5$CH$_2$O

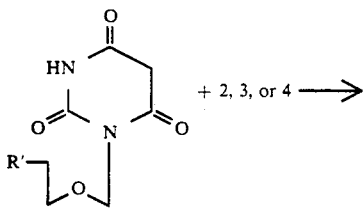

11. R' = OCOCH$_3$
12. R' = OH

EXAMPLE 3

Synthesis of 5-benzyl
1-[(1,3 hydroxy-2-propoxy)methyl] barbiturates

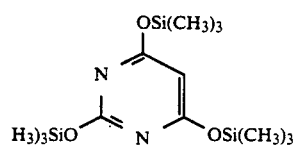

9

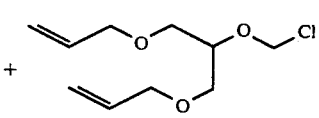

22

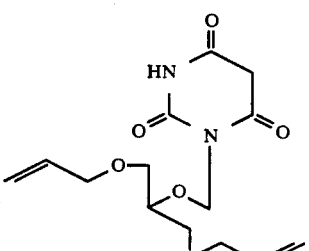

23 aldehyde 2, 3, or 4

-continued
Synthesis of 5-benzyl
1-[(1,3 hydroxy-2-propoxy)methyl] barbiturates

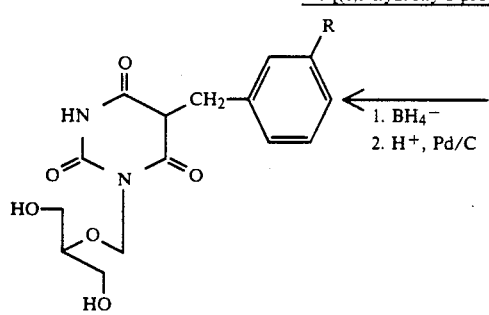

27 R = H
28 R = CH₃O
29 R = C₆H₅CH₂O

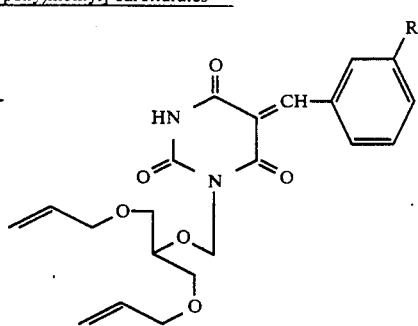

24 R = H
25 R = CH₃O
26 R = C₆H₅CH₂O

The preparation of these achiral derivatives 27-29 is patterned after the chemistry presented in Examples 1 and 2, above. Compound 9, the persilyated derivative of barbituric acid, is reacted with the methyl ether of 1,3-diallyl glycerol (22). Usually, the chloromethyl ether of 1,3-dibenzylglycerol (MacCoss et al., vol. 26, *Chem. Scriota.* pp. 113-121 (1986) and Kim et al., *Chem. Lett.* pp. 1045-1048 (1988)) is condensed with a persilyated heterocycle, but to avoid "reduction" problems, i.e., with 29, the chloromethyl ether of 1,3-diallylglycerol is used. This reagent can be made in the same way as 1,3-dibenzylglycerol (MacCoss et al., vol. 26, *Chem. Scripta.* pp. 113-121 (1986)) by treating chloroepihydrin with sodium allyloxide. Compound 23, the product from the reaction of 9 and 22 is then subjected to similar chemistry as described in Examples 1 and 2A for attachment of the benzyl groups. Reduction of the arylidenes 24-26 with sodium borohydride at room temperature will not affect the allyl ether protecting groups (Pelter et al., "Boron-Hydrogen Compounds" in vol. 3, *Comprehensive Organic Chemistry* pp. 760-772 (D. N. Jones, Ed., Pergamon Press, New York 1979). These groups can be conveniently removed in methanol with a trace amount of p-toluenesulfonic acid and a catalytic amount of palladium on activated charcoal to yield the products 27-29. Benzyl ethers are stable under these cleavage conditions (Boss et al., vol. 15, *Angew Chem. Inter. Ed. Engl.*, pp. 558-559 (1976)).

An alternate approach to 27-29 involves alkylation of 19-21 with 22, followed by deprotection using the methods disclosed above.

EXAMPLE 4

Synthesis of 5-benzyl
1-[(1,3-aminohydroxy)ethoxy] methyl barbiturates

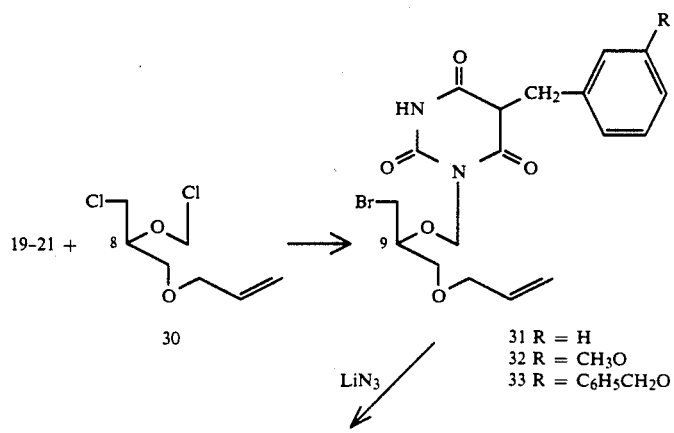

31 R = H
32 R = CH₃O
33 R = C₆H₅CH₂O

-continued
Synthesis of 5-benzyl
1-[(1,3-aminohydroxy)ethoxy] methyl barbiturates

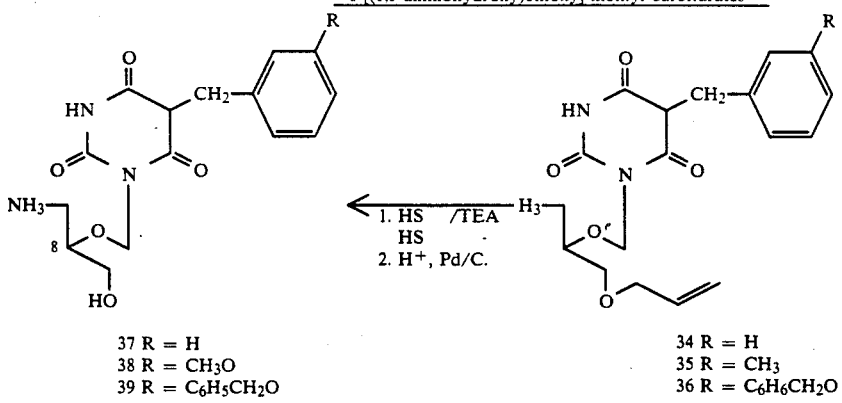

37 R = H
38 R = CH₃O
39 R = C₆H₅CH₂O

34 R = H
35 R = CH₃
36 R = C₆H₆CH₂O

The pathway illustrated here describes the synthesis of the [(1-amino,3-hydroxy)ethyl]methyl tail. However, the other chiral derivative, (1-hydroxy,3-amino)ethoxy]methyl tail, also is produced by this protocol.

Treatment of 19-21, the persilyated 5-benzyl derivatives, with the S-chloromethyl ether 30 should provide the respective acyclonucleosides 31-33 in good yields. The bromo derivatives 31-33 are next reacted with LiN₃ in DMF to yield azidoderivatives 34-36. These derivatives are then reduced and deprotected to furnish the targeted, chiral aminomethyl analogues 37-39. The reduction of the azido group is carried out using propane-1,3-dithiol in the presence of triethylamine (TEA). This reduction is selective for azido groups and will not affect any of the other function groups on 34-36 (Bayley et al., *Tetrahedron Lett.*, pp. 3633-3634 (1978)). This procedure has worked well in the reduction of alkyl azides in our laboratory, as does sodium borohydride (Rolla, F. J., vol. 47, *Org. Chem.* pp. 4327-432 (1982)). The allyl ether is removed as described previously for the deblocking of 24-26 (Example 3).

EXAMPLE 5

Synthesis of 5-benzyl
1-[(2-(3-carboxypropionyloxy)ethoxy)methyl] barbiturates

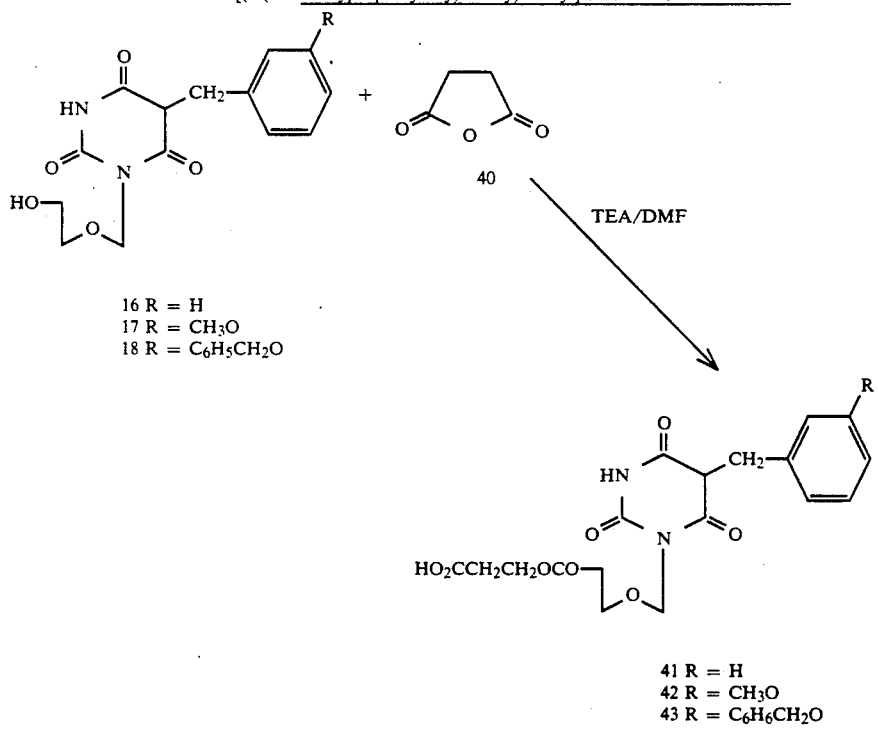

16 R = H
17 R = CH₃O
18 R = C₆H₅CH₂O

41 R = H
42 R = CH₃O
43 R = C₆H₆CH₂O

Compounds 16-18 are combined with succinic anhydride (40) in the presence of triethylamine and DMF and heated. After cooling and removing DMF by evaporation, the residue is taken up in water, adjusted to pH 2 and run over a small silica column, following the procedure of Chu et al., vol. 24, *J. Heterocyclic Chem.* pp. 1651-1656 (1986), to produce the succinate derivatives 41-43.

EXAMPLE 6

Biological Evaluation

The activity of the 5-benzyl barbiturates of this invention as inhibitors of uridine phosphorylase was measured essentially following the procedure of Naguib et al. (vol. 36, *Biochem. Pharmac.* pp. 2195-2201 (1987)), the disclosure of which is incorporated herein by reference. An abridged description of the protocol is described below.

Mouse livers for these experiments were obtained from Swiss Albino (CD1) mice (Charles River Laboratories, Boston, Mass.). The mice were killed by cervical dislocation, and the livers removed and washed with ice-cold normal saline (0.9%) before any further manipulation.

The saline solution was wiped off the organs with tissue paper, and the organs weighed and then cut into smaller pieces in ice-cold homogenization buffer (3:1, v/w) containing 20 mM potassium phosphate (pH 8), 1 mM EDTA, and 1 mM mercaptoethanol. The livers were then homogenized with a polytron homogenizer (Brinkman), and the homogenates centrifuged at 105,000 g for 1 hr at 4°. The supernatant fluids (cytosol) were collected and used as the enzyme source.

The assay mixture contained 20 mM potassium phosphate (pH 8), 1 mM EDTA, 1 mM mercaptoethanol, substrate (uridine, 9 mCi/mmol) and 40 µl of enzyme preparation in a final volume of 80 µl. Under these conditions the activity was linear with time and amount of enzyme. Apparent $K_i$ values were estimated from Dixon plots (1/v vs[I]) of the data by a computer program with least squares fitting, using uridine (1 mM) and five different concentrations of the inhibitor within the range of 0.0625 µM and 1.0 µM.

Incubation was carried out at 37° C., for 30 min. The reaction was terminated by immersing the reaction tubes (1 ml Eppendorf tubes) in boiling water for 1 min. and then freezing the reaction tubes for at least 20 min. Proteins were removed by centrifugation, and 5 µl of the supernatant fluid spotted on silica gel TLC plates which had been prespotted with 5 µl of a standard mixture of 10 mM each uridine and uracil. The plates were then developed in a mixture of chloroform and methanol (90:10, v/v). Uridine and uracil were identified by UV quenching. (Rf values for uridine and uracil are 0.09 and 0.39, respectively.) Spots were then cut out and counted in 20 ml of Omnifluor-based scintillant.

Protein concentrations were determined by the method of Bradford, (Bradford, M. M., vol. 72, *Analyt. Biochem.* p. 248 (1976)) as described by the Bio-Rad Laboratories (Bio-Rad Laboratories, *Bulletin* 1069, Bio-Rad Laboratories, Richmond, Calif. (1979)), using bovine λ-globulin as a standard.

Table 1, presented below, shows the apparent inhibition constants (app. Ki values, using a uridine substrate concentration of 1 mM) for the inhibition of uridine phosphorylase, determined for four compounds of the present invention, their analogous acyclouridine counterparts, barbituric acid (barbiturate), and 5-benzyl barbiturate. Table 1 also shows the solubilities of the various compounds in water at room temperature.

TABLE I

| Compounds: | APP $K_i$ (µM): | SOL. (mM) |
|---|---|---|
| BU | 54.0* | ≦1 |
| BBU | 9.2* | ≦1 |
| BAU | 3.2 | 1 |
| BBAU | 1.1 | ≦1 |
| Barbiturate | ~1500 | >3 |
| 5-benzyl barbiturate (BB) | 44.0 | >3 |
| 5-benzyloxybenzyl barbiturate (BBB) | 3.0 | >3 |
| 5-benzyloxybenzyl-1-[(1-hydroxy-2-ethoxy)methyl] barbiturate (BBAB) | 0.8 | >3 |
| 5-benzyloxybenzylacetyl-1-[(1-hydroxy-2-ethoxy)methyl] barbiturate (BBCAB) | 2.6 | >3 |
| 5-Methoxybenzylacetyl acyclo barbiturate (MBCAB) | 1.9 | >3 |

*calculated from Niedzwicki, J. G. et al., vol. 31, Biochem. Pharmac., pp. 1857-1861 (1982).
in water, at room temperature.

Previous studies have shown that the presence of a second benzyl ring at the 5 position of the uracil group and the addition of the acyclo tail increases the binding affinity of these compounds for uridine phosphorylase. (Niedzwicki et al., vol. 31, *Biochem. Pharmac.*, pp. 857-861 (1982)). However, this renders the uridine phosphorylase inhibitors of the art relatively insoluble in aqueous solutions (≦1 mM, in water at room temperature), and therefore difficult to manipulate for many medical applications. In addition, the compounds are difficult and expensive to synthesize.

As can be seen from the results in Table I, each of the barbiturate derivatives exhibits stronger inhibition of uridine phosphorylase than its uracil counterpart. For example, 5-benzyloxybenzyl barbiturate (BBB) is a significantly stronger uridine phosphorylase inhibitor than BBU (5-benzyloxybenzyl uracil). The addition of an acyclo tail to the benzyloxybenzyl barbiturate further improves inhibition, (compare BBAB (5-benzy]Oxybenzyl-1-[(1-hydroxy-2-ethoxy)methyl] barbiturate) with BBAU (5-benzyl-oxybenzyl-acyclouridine)). Moreover, the water solubility of BBAB and the other 5-benzyl barbiturates shown is significantly greater than that of the acyclouridines (≧3 mM in water, at room temperature).

It is clear that the compounds of this invention have uridine phosphorylase inhibition activity equal to, or greater than, that of their acyclouridine counterparts. However, their superior water solubility provides them with even greater potency than the compounds of the art in clinical applications. In addition, the potency of the benzylbarbiturate derivates may be increased further by modifications to include the hydroxymethyl (HM-) or the aminomethyl (AM-) tail (See Synthesis Examples 3 and 4).

It should be clear that various modifications, additions and subtractions can be made without departing from the spirit or scope of the invention. For example, it should be appreciated that the present invention can also be employed in conjunction with other chemotherapeutical or biological response-modifying agents. For example, the antiviral combination therapy of the present invention can be employed in tandem with the administration of bone marrow stimulating factors, such as granulocyte-macrophage colony stimulating factors (GM-CFSs), other colony stimulating factors, erythopoietin (EPO), and other materials which stimulate hematopoietic activity. (For a further discussion of GM-CSF activity, see Hammer et al., vol 31, *Antimicrobial Agents and Chemotherapy*, pp. 1046-1050 (1987)). Similarly, the combination therapy of the present invention can be undertaken in conjunction wth efforts to stimulate the immune system, such as the administration of interferons (e.g., alpha-A interferon) or other lymphokines.

In a similar manner, combination therapies of the present invention for the treatment of cancer can include other chemotherapeutic compounds such as methotrexate, N-(phosphonoacetyl)-L-aspartate, and allopurinol.

What is claimed is:

1. A compound represented by the general formula:

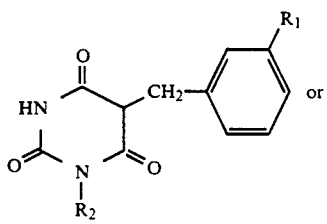

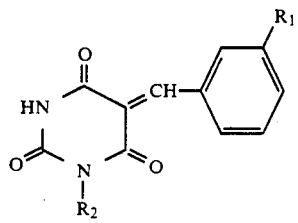

where
$R_1 = OCH_2C_6H_5$, and
$R_2 = H$, or an acyclotail of the general formula:

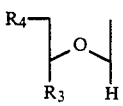

where
$R_3 = H$, $CH_2OH$, or $CH_2NH_2$, and
$R_4 = OH$, $NH_2$, or $OCOCH_2CH_2CO_2H$.

2. The compound of claim 1 which is 5-benzyloxybenzyl barbiturate (BBB).

3. The compound of claim 1 which is 5-benzyloxybenzyl-1-[(1-hydroxy-2-ethoxy)methyl] barbiturate (BBAB).

4. The compound of claim 1 which is 5-benzyloxybenzylacetyl-1-[(1-hydroxy-2-ethoxy)methyl] barbiturate (BBCAB).

5. The compound of claim 1 which is 5-benzyloxybenzyl-1-[(1,3 dihydroxy-2-propoxy)methyl] barbiturate (HM-BBAB).

6. The compound of claim 1 which is 5-benzyloxybenzyl-1-[(1-hydroxy, 3 amino-2 propoxy)methyl] barbiturate (AM-BBAB).

7. The compound of claim 1 which is 5-benzyloxybenzyl-1-[(2-(3-carboxy propionyloxy)ethoxy)methyl] barbiturate (succ-BBAB).

8. A compound represented by the general formula:

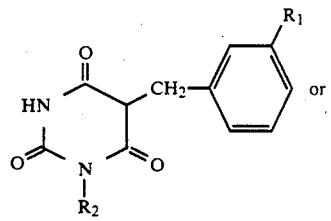

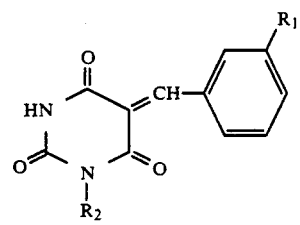

where
$R_1$ is H or $OCH_3$, and
$R_2$ is an acyclotail of the general formula:

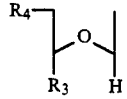

where
$R_3 = H$, $CH_2OH$, or $CH_2NH_2$, and
$R_4 = OH$, $NH_2$, or $OCOCH_2CH_2CO_2H$.

9. The compound of claim 8 which is 5-benzyl-1-[(1-hydroxy-2-ethoxy)methyl] barbiturate (BAB).

10. The compound of claim 8 which is 5-methoxybenzylacetyl barbiturate (MBCB).

11. The compound of claim 8 which is 5-benzyl-1-[(1,3 dihydroxy-2-propoxy)methyl] barbiturate (HM-BAB).

12. The compound of claim 8 which is 5-benzyl-1-[(1-hydroxy, 3 amino-2-propoxy)methyl] barbiturate (AM-BAB).

13. The compound of claim 8 which is 5-benzyl-1-[(2-(3-carboxy propionyloxy)ethoxy)methyl] barbiturate (succ-BAB).

14. A method for improving the effectiveness of antiviral pyrimidine nucleoside compounds in the treatment of viral infections, in which treatment is accompanied by the side effect of nucleoside toxicity in uninfected cells, the method comprising the steps of administering to an infected subject an antiviral pyrimidine nucleoside compound in an amount effective to disrupt viral replication in infected cells, and a 5-benzyl barbiturate in an amount effective to decrease nucleoside toxicity in uninfected cells.

15. A method of reducing the anemia caused by administration of an antiviral pyrimidine nucleoside compound, said method comprising the administration of a 5-benzyl barbiturate.

16. The method of claim 14 or 15 wherein the method further includes administering uridine in an amount effective to raise plasma uridine levels.

17. A pharmaceutical preparation comprising an antiviral pyrimidine nucleoside compound in an amount effective to disrupt viral replication in virus-infected cells and a 5-benzyl barbiturate in an amount effective to reduce nucleoside toxicity in uninfected cells.

18. The pharmaceutical preparation of claim 16 wherein the 5-benxyl barbiturate has a uridine phosphorylase inhibition constant $K_i$ less than about 0.4 µM and having a solubility greater than 3 mM in water at room temperature.

19. The pharmaceutical preparation of claim 16 wherein said 5-benzyl barbiturate is 5-benzyloxybenzyl barbiturate (BBB).

20. The pharmaceutical preparation of claim 16 wherein said 5-benzyl barbiturate is 5-benzyl-1-[(1-hydroxy-2-ethoxy)methyl] barbiturate (BAB).

21. The pharmaceutical preparation of claim 16 wherein said 5-benzyl barbiturate is 5-benzyloxybenzyl-1-[(1-hydroxy-2-ethoxy)methyl] barbiturate (BBAB).

22. The pharmaceutical preparation of claim 16 wherein said 5-benzyl barbiturate is 5-benzyloxybenzylacetyl-1-[(1-hydroxy -2-ethoxy)methyl] barbiturate (BBCAB).

23. The pharmaceutical preparation of claim 16 wherein said 5-benzyl barbiturate is 5-methoxybenzylacetyl barbiturate (MBCB).

24. The pharmaceutical preparation of claim 16 wherein said 5-benzyl barbiturate is 5-benzyl-1-[(1,3 dihydroxy-2-propoxy)methyl] barbiturate (HM-BAB).

25. The pharmaceutical preparation of claim 16 wherein said 5-benzyl barbiturate is 5-benzyloxybenzyl-1-[(1,3 dihydroxy-2-propoxy)methyl] barbiturate (HM-BBAB).

26. The pharmaceutical preparation of claim 16 wherein said 5-benzyl barbiturate is 5-benzyl-1-[(1-hydroxy, 3 amino-2-propoxy)methyl] barbiturate (AM-BAB).

27. The pharmaceutical preparation of claim 16 wherein said is 5-benzyl barbiturate 5-benzyloxybenzyl-1[(1-hydroxy, 3 amino-2 propoxy)methyl] barbiturate (AM-BBAB).

28. The pharmaceutical preparation of claim 16 wherein said 5-benzyl barbiturate is 5-benzyl-1-[(2-(3-carboxy propionyloxy)ethoxy)methyl] barbiturate (succ-BAB).

29. The pharmaceutical preparation of claim 16 wherein said 5-benzyl barbiturate is 5-benzyloxybenzyl-1-[(2-(3-carboxy propionyloxy)ethoxy)methyl] barbiturate (succ-BBAB).

30. A method for improving the effectiveness of 5-fluorouracil in the treatment of cancerous cell growth in a subject, which treatment is accompanied by the side effect of nucleoside toxicity in non-tumor cells, comprising the steps of administering 5-fluorouracil to said subject in an amount effective to inhibit DNA or RNA replication in tumor cells, and a 5-benzyl barbiturate in an amount effective to decrease nucleoside toxicity in non-tumor cells.

31. A method of increasing the efficacy of halogenated uridine compounds for use in cancer chemotherapy, said method comprising the step of administering a 5-benzyl barbiturate in an amount effective to substantially reduce the catabolism of said uridine compounds.

32. The method of claim 31 wherein said amount of 5-benzyl barbiturate is sufficient to reduce nucleoside toxicity in non-tumor cells.

33. The method of claim 30 or 31 further comprising the step of administering uridine in an amount effective to raise plasma uridine levels.

34. The method of claim 30 or 31 further comprising the step of administering uracil in an amount effective to raise plasma uridine levels.

35. A pharmaceutical preParation for use in cancer chemotherapy comprising a halogenated uridine compound in an amount effective to inhibit DNA or RNA synthesis, and a 5-benzyl barbiturate in an amount effective to substantially reduce the catabolism of said halogenated uridine compound.

36. The preparation of claim 35 further comprising uridine in an amount effective to raise plasma uridine levels.

37. The preparation of claim 35 further comprising uracil in an amount effective to raise plasma uridine levels.

38. A uridine phosphorylase inhibitor having a $K_i$ less than about 0.2 µM, and having a solubility greater than 3 mM in water at room temperature.

* * * * *